US010335165B2

(12) United States Patent
Schreider (10) Patent No.: US 10,335,165 B2
(45) Date of Patent: Jul. 2, 2019

(54) BONE PUNCH WITH SECURE PUNCHING SLIDE

(71) Applicant: Christoph Zepf, Dürbheim (DE)

(72) Inventor: Sergej Schreider, Rottweil (DE)

(73) Assignee: Christoph ZEPF, Dürbheim (DE)

( * ) Notice: Subject to any disclaimer, the term of this patent is extended or adjusted under 35 U.S.C. 154(b) by 239 days.

(21) Appl. No.: 15/278,504

(22) Filed: Sep. 28, 2016

(65) Prior Publication Data

US 2017/0086858 A1 Mar. 30, 2017

(30) Foreign Application Priority Data

Sep. 29, 2015 (DE) .................... 20 2015 006 833 U (51) Int. Cl.
*A61B 17/16* (2006.01)
*A61B 17/29* (2006.01)

(52) U.S. Cl.
CPC ... *A61B 17/1611* (2013.01); *A61B 2017/2936* (2013.01)

(58) Field of Classification Search
CPC ........ A61B 17/1604–17/1611; A61B 17/1657; A61B 17/1659
See application file for complete search history.

(56) References Cited

U.S. PATENT DOCUMENTS

| 268,344 | A | * | 11/1882 | Wood ...................... B25B 23/12 81/125 |
| 5,009,661 | A | * | 4/1991 | Michelson ......... A61B 17/1608 606/170 |
| 5,026,375 | A | | 6/1991 | Linovitz et al. |
| 5,273,519 | A | | 12/1993 | Koros et al. |
| 5,451,227 | A | * | 9/1995 | Michaelson ....... A61B 17/1611 606/170 |
| 5,569,258 | A | * | 10/1996 | Gambale ............ A61B 17/1611 606/167 |
| 5,584,844 | A | | 12/1996 | Weisshaupt |

(Continued)

FOREIGN PATENT DOCUMENTS

DE 43 16 769 C1 5/1994
DE 43 16 768 A1 11/1994
(Continued)

Primary Examiner — Matthew J Lawson
Assistant Examiner — Amy R Sipp
(74) Attorney, Agent, or Firm — McGlew and Tuttle, P.C.

(57) ABSTRACT

A bone punch includes a base body with a guide shaft (3), a handle (4) and a punching slide (8) supported adjustably along an upper guiding surface (13) of the guide shaft (3). An actuating lever (6) with an adjusting lever (65) interacts with the punching slide (8) for adjustment against a spring action of a restoring spring (46). In a distal end area (10), the punching slide (8) has a securing element (45), which extends between two side walls (25, 26) of the punching slide (8) on the guide shaft (3). The securing element (45) has two laterally protruding positive-locking elements (51, 52). Each side wall (25, 26) is provided with an inner, distally limited longitudinal groove (40, 41) running in the longitudinal direction (9) of the guide shaft (5). Each positive-locking element (51, 52) is longitudinally displaceably inserted into a respective one of the grooves (40, 41).

20 Claims, 9 Drawing Sheets

(56) References Cited

U.S. PATENT DOCUMENTS

| | | | | |
|---|---|---|---|---|
| 5,851,214 A | * | 12/1998 | Larsen | A61B 17/1608 606/170 |
| 7,655,020 B2 | | 2/2010 | Wenzler et al. | |
| 2003/0216740 A1 | * | 11/2003 | Michelson | A61B 17/1611 606/83 |
| 2006/0085021 A1 | * | 4/2006 | Wenzler | A61B 17/1611 606/184 |
| 2006/0111737 A1 | * | 5/2006 | Wenzler | A61B 17/1611 606/184 |
| 2006/0122615 A1 | * | 6/2006 | McKinley | A61B 17/1611 606/83 |
| 2008/0221606 A1 | * | 9/2008 | Faulhaber | A61B 17/1611 606/184 |
| 2010/0114139 A1 | * | 5/2010 | Zepf | A61B 17/1611 606/184 |
| 2011/0071563 A1 | * | 3/2011 | Magliani | A61B 17/1611 606/205 |
| 2013/0041379 A1 | * | 2/2013 | Bodor | A61B 17/1611 606/83 |
| 2016/0287282 A1 | * | 10/2016 | Ferro | A61B 17/295 |

FOREIGN PATENT DOCUMENTS

| | | |
|---|---|---|
| DE | 295 00 422 U1 | 4/1995 |
| DE | 20 2004 017 974 U1 | 1/2005 |
| DE | 10 2009 056 099 B4 | 4/2012 |
| WO | 96/39 959 A1 | 12/1996 |

\* cited by examiner

BONE PUNCH WITH SECURE PUNCHING SLIDE

CROSS REFERENCE TO RELATED APPLICATIONS

This application claims the benefit of priority under 35 U.S.C. § 119 of German Utility Model 20 2015 006 833.2 filed Sep. 29, 2015, the entire contents of which are incorporated herein by reference.

FIELD OF THE INVENTION

The present invention pertains to a bone punch with a base body, which consists of a guide shaft, a handle, which is arranged in a fixed and angled manner on the guide shaft, and with a punching slide, which is supported adjustably along the guide shaft on an upper guiding surface of the guide shaft, which guiding surface is located opposite the handle, and with an actuating lever, which is pivotably mounted in a connection area of the handle to the guide shaft between two side walls which are spaced apart from one another, wherein the actuating lever forms an adjusting lever, via which the actuating lever operatively interacts with the punching slide for the adjustment thereof along the guide shaft against the spring action of a restoring spring, and wherein the punching slide is guided adjustably along on the guide shaft via guide elements, which have a T-shaped profile, engage one another in a positive-locking manner and are detachable by longitudinal displacement.

BACKGROUND OF THE INVENTION

A bone punch of the type of this class, which is called a surgical punching instrument, is known from DE 20 2004 017 974 U1 (and corresponding U.S. Pat. No. 7,655,020). This prior-art bone punch has a guide shaft, at which a handle is arranged in a fixed manner, which runs angled to the guide shaft. Furthermore, an actuating lever, which is pivotably mounted in this connection area, is provided in the area of transition from the guide shaft to this handle. In this connection area or in the area of the pivotable mounting of the actuating lever, the connection area forms two side walls, which are spaced apart from one another, between which the actuating lever protrudes through with an adjusting lever and extends on the top over the planar guiding surface of the guide shaft in the normal operating state.

In this connection, this adjusting lever of the actuating lever operatively interacts with a recess of a punching slide, which is open downwards toward the guide shaft. The punching slide has a "lower" sliding surface toward the punching slide, with which the punching slide is arranged longitudinally displaceably on the guide shaft. Guide elements, which have a T-shaped profile and engage one another in a positive-locking manner, are provided for the secure hold of the punching slide on the guide shaft. Because of a special configuration of the mounting of the actuating lever between the two side walls the actuating lever can be "retracted" from its active position with its adjusting lever engaging with the punching slide, so that the adjusting lever no longer operatively interacts with the punching slide. In this "retracted" position of the actuating lever the punching slide can be returned distally along the guide shaft until the guide elements of the punching slide and of the guide shaft become disengaged. In this position, the punching slide can thus be completely removed from the guide shaft in a simple manner, since there is no longer any connection between these parts. The guide shaft, the connection area and the handle thereby form a type of base body.

In this connection, the subject of DE 20 2004 017 974 U1 is based on surgical punching instruments according to DE 43 16 768 A1, DE 43 16 769 C1, DE 295 00 422 U1, U.S. Pat. Nos. 5,026,375, 5,273,519, 5,569,258 as well as WO 96/39 959.

In these bone punches or punching instruments, the restoring springs for the actuating lever have a leaf-spring configuration and act as restoring springs between the fixed handle and the actuating lever. Since the assembly and disassembly are difficult in these prior-art restoring spring systems, such restoring springs may make the handling of such a punching instrument or such a bone punch difficult, since these springs may weaken or may not apply the necessary restoring force to ensure a proper functioning of the punching instrument. Furthermore, these restoring springs cannot be readily removed from one another or from the respective handle or actuating lever to which they are fastened.

Based on these leaf spring configurations, a restoring spring in the form of a compression coil spring (axial compression spring), which is arranged and guided at least partially in a guide groove of the sliding surface of the punching slide by means of a guide pin axially passing through the restoring spring, is used in the subject of DE 20 2004 017 974 U1. A distal stop surface, which is rigidly connected to the punching slide, is provided as a step bearing for the rear distal spring end of the restoring spring. Furthermore, with its front proximal end in case of a removed punching slide, the restoring spring is in contact with a proximal stop surface of the punching slide. The restoring spring is in contact with a proximal stop surface of the guide shaft itself in the case of an ergonomically assembled punching slide.

This means that the restoring spring in this configuration is an integral component of the guide shaft and of the punching slide, so that it is not outwardly visible. When the punching slide is removed from the guide shaft, this restoring spring is automatically not operatively interacting, so that especially the assembly and disassembly of the punching slide on the guide shaft are considerably simplified.

However, it has been recently desired that after detaching the guide elements the punching slide can be separated from the base body consisting of the guide shaft, the connection area and the handle, but the punching slide and the base body still remain in connection with one another in some way, so that these two parts cannot be completely separated from one another and, for example, can be cleaned together. Since especially a plurality of bone punches shall be cleaned in a joint cleaning process, such a secure "securing" has the advantage that the components of a bone punch belonging together can always be correctly reassembled.

In this respect, a bone punch, called a surgical instrument, is known from DE 10 2009 056 099 B4, in which such a mode of operation is provided after separating the punching slide from the guide shaft or from the base body. This is achieved in this subject by the punching slide, in the position separated from the guide shaft, being arranged pivotably at the guide shaft. The guide shaft has, for this purpose, at its proximal end an elongated hole, in the area of which the punching slide has two side walls, which are spaced apart from one another laterally and protrude downwards to above the elongated hole and which are in connection with the mounting pin, which in turn extends through the elongated hole. In this case, this mounting pin is configured as a type of screw and is connected to the two side walls in a fixed manner. Provisions are thereby made for the guide shaft or the base body to have a reduced width in the area adjacent to the elongated hole so that the two side walls do not project laterally beyond the guide shaft or the connection area of the guide shaft to the handle.

In this configuration, the "securing means" are in the form of the elongated hole as well as of the two side walls with the securing pin freely accessible from outside, so that these may become contaminated. Furthermore, a special configuration of the connection area between the guide shaft and the handle is provided here, since this elongated hole must extend distally rearward over a considerable path of adjustment in the longitudinal direction of the guide shaft.

SUMMARY OF THE INVENTION

Accordingly, a basic object of the present invention is to create a bone punch with a guide shaft and with a punching slide, especially based on DE 20 2004 017 974 U1, in which, after separating the guide elements between the guide shaft and the punching slide, the punching slide along with its sliding surface can be removed from the guiding surface of the guide shaft, but continues to remain especially pivotably movably in connection with the guide shaft or with the connection area of the guide shaft to the handle.

This object is accomplished according to the present invention by the punching slide having in a the punching slide distal area a securing element, which protrudes between the two side walls in the assembled state of the punching slide on the guide shaft, and that the securing element has two laterally protruding positive-locking elements, and that each side wall is provided with an inner longitudinal groove, which is distally limited and runs in the longitudinal direction of the guide shaft and into which a positive-locking element each can be inserted in a longitudinally displaceable manner.

Due to the configuration according to the present invention, a bone punch is provided, in which after separating the guide elements between the guide shaft and the punching slide, the punching slide continues to remain at least pivotably movably in connection with the guide shaft or with the connection area between the guide shaft and the handle or with the handle. In this connection, the securing element of the punching slide and the corresponding, inner longitudinal grooves in the area of the side walls of the base body are arranged such that these are not externally accessible in the normal operating state of the bone punch according to the present invention. Correspondingly, the bone punch according to the present invention has the same outward appearance in the normal, assembled, operating state as the bone punch configured according to the closest state of the art of DE 20 2004 017 974 U1.

Provisions may thus be made according to an aspect of the invention for the securing element to have a bearing section, which extends toward the punching slide and with which the securing element is detachably in connection with the punching slide. For example, a screw connection may be provided here for the detachable connection. This screw connection is especially accessible from outside when the punching slide is detached from the base body, so that the punching slide can be separated entirely from the securing element and thus from the base body as needed after loosening the screw connection.

The configuration according to an aspect of the invention is guided by the subject of DE 20 2004 017 974 U1 (corresponding U.S. Pat. No. 7,655,020 which is hereby incorporated by reference in its entirety) as the starting point. The combination of features according to this aspect may be provided as an alternative configuration to a screw connection between the punching slide and the securing element. After that, an axial compression spring, which is arranged on a guide pin and is partially arranged in a lower mounting groove of the punching slide in the assembled state, is provided as a restoring spring, wherein the guide pin, in the assembled state, is removably inserted proximally into a mounting hole of the punching slide and distally into a second hole of the punching slide. Furthermore, the axial compression spring is axially supported at a first stop of the punching slide when the punching slide is removed from the guide shaft, the axial compression spring being supported axially at a distal second stop of the punching slide. The axial compression spring is consequently mounted between these two stops, wherein the stops are formed at least partially by the mounting groove. In this alternative configuration, the securing element is mounted with its bearing section between the distal end of the axial compression spring and the second stop. The assembly and disassembly of the securing element are made easier by this configuration, since no screw connection is to be provided, but rather the securing element with its bearing section is simply mounted "in a clamping manner" between the axial compression spring and the distal stop. During the insertion of the guide pin together with the axial compression spring, similar to an embodiment variant of the subject of DE 20 2004 017 974 U1, the securing element together with the guide pin and the axial compression spring is correspondingly mounted at the same time on the punching slide in the area of the mounting groove because of the arrangement of the securing element with its bearing section, which is then likewise arranged on the guide pin in the distal end area of the axial compression spring.

For further simplification of the assembly, provisions may be made according to an aspect of the invention for the guide pin to have in its distal end area a radially protruding stop collar, via which the axial compression spring is axially supported indirectly at the second, distal stop of the punching slide, and for the securing element with its bearing section to be mounted on the guide pin between the distal end of the axial compression spring and the stop collar of the guide pin. By means of this configuration, the securing element with its bearing section is fixed on the guide pin between the distal end of the axial compression spring and the stop collar of the guide pin already before assembly, so that the joint handling thereof can take place in a correspondingly simple manner.

Further, provisions may be made according to an aspect of the invention for the first, proximal stop to be part of a first coupling element of the punching slide, which coupling element has a T-shaped configuration and which projects toward the guiding surface of the guide shaft over the sliding surface of the punching slide and engages in a longitudinally displaceable manner with a mounting groove, which has a T-shaped configuration, in the assembled state, and for the second, distal stop to be part of a second coupling element of the punching slide, which coupling element has a T-shaped configuration and which projects toward the guiding surface of the guide shaft over the sliding surface of the punching slide and engages in a longitudinally displaceable manner with inner longitudinal grooves arranged laterally in the side walls in the assembled state, and for the two stops to be at the same time also part of the mounting groove of the punching slide for the axial compression spring. Because of this configuration, the guide pin together with the securing element and the axial compression spring can be inserted between the two stops in a simple manner. The two coupling elements may have locking forks which are "open," for example, toward the guide shaft for mounting the guide pin and into which the guide pin can be inserted in a locking and axially non-displaceable manner.

Due to the configuration according to an aspect of the invention, the guide pin can, in an extremely simple manner, be assembled and disassembled together with the securing element placed on the guide pin, as well as with the axial compression spring pushed onto the guide pin. After that, provisions may be made for the punching slide to be provided with a mounting hole in the area of its first, proximal coupling element, into which mounting hole the guide pin can be inserted with a proximal plug pin with a radially tapered configuration, and for the punching slide to have a through hole in the area of its second, distal coupling element, and for the guide pin to have, in distal, axial extension to its stop collar, a locking pin with a radially tapered configuration, with which the guide pin can be engaged with the through hole in the area of the second coupling element in a positive-locking manner by means of an axial adjustment of the guide pin in the mounting hole against the spring action of the axial compression spring placed on the guide pin. By means of this configuration, the guide pin is held securely on the two coupling elements in the area of the two stops and cannot by itself become detached even during the operation and even in case of the punching slide "removed" from the guide shaft.

The present invention is explained in examples in detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
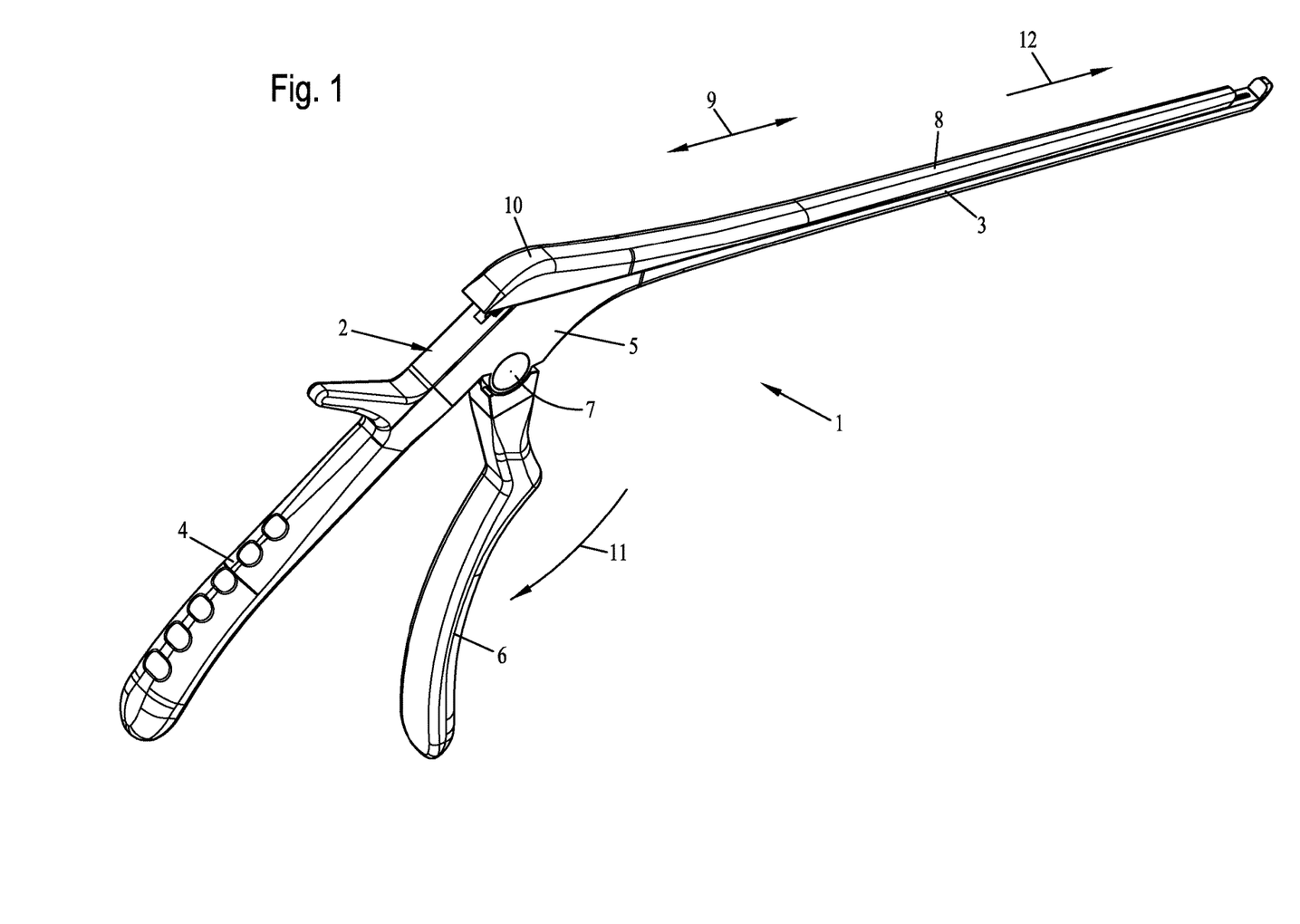
FIG. 1 is a perspective view of a bone punch according to the present invention in the normal, assembled operating state.

Referring to the drawings, FIG. 1 shows a perspective view of a bone punch 1. This bone punch 1 has a base body 2, which consists essentially of a guide shaft 3, a handle 4, as well as a connection area 5 provided between the handle 4 and the guide shaft 3. An actuating lever 6 is pivotably mounted in this connection area 5, for which a corresponding mounting pin 7 is provided. The special configuration, especially in reference to the configuration of the mounting pin 7 and the special mounting of the actuating lever 6, can be taken from DE 20 2004 017 974 U1, to which reference is herewith made to its full extent. This means that the mounting of the actuating lever 6 in the connection area 5 is preferably configured identically as in the subject of DE 20 2004 017 974 U1 in the embodiment variant of the bone punch 1.

Further, it can be seen from FIG. 1 that on the guide pin is arranged a punching slide 8, which is configured as adjustable in the longitudinal direction of the double arrow 9 along the guide shaft 3. With its distal end area 10, the punching slide 8 operatively interacts with an adjusting lever of the actuating lever 6, which adjusting lever cannot be seen from FIG. 1, so that upon actuation of the actuating lever 6 in the direction of arrow 11, the punching slide 8 is adjusted in the direction of arrow 12, as this is known from the state of the art.

Figure 2:
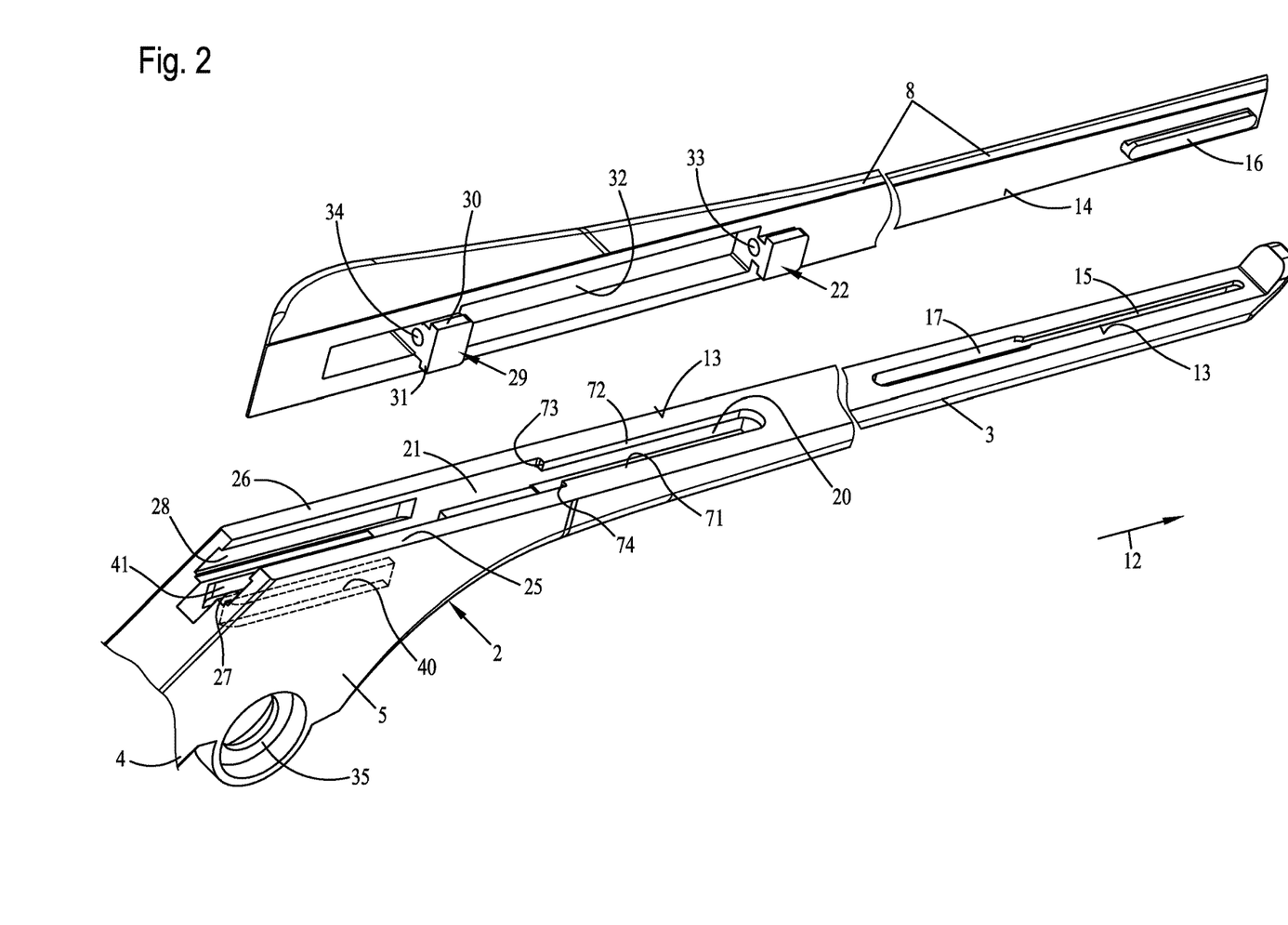
FIG. 2 is a perspective partial view of the base body of the bone punch from FIG. 1, comprised of the guide shaft, the connection area and the handle, as well as a perspective bottom view of the punching slide each in shortened view.

FIG. 2 shows a perspective exploded view of the base body 2 with its guide shaft 3, along with the connection area 5 and a part of the handle 4 in a perspective top view as well as in a perspective bottom view of the punching slide 8, both the guide shaft 3 and the punching slide 8 being shown shortened in their length.

It can be seen that the guide shaft 3 has a planar guiding surface 13 which is located "on the top" opposite the handle which is arranged obliquely downwards on the guide shaft 3, on which guiding surface the punching slide 8 lies in a longitudinally displaceable manner with a lower sliding surface 14 in the assembled operating state shown in FIG. 1. In the area of the guiding surface 13, the guide shaft 3 has in its proximal end area a mounting groove 15 with a T-shaped configuration, which can operatively interact with a guide strip 16 of the punching slide 8, which guide strip has a T-shaped configuration and protrudes over the sliding surface 14 downwards toward the guide shaft 3. In order to be able to engage the guide strip 16 with the mounting groove 15, a laterally expanded insertion groove 17 is connected distally to the mounting groove 15, into which insertion groove the guide strip 16 can be inserted. After inserting the guide strip 16 into the insertion groove 17 and after adjusting the punching slide 8 in the direction of arrow 12, the T-shaped guide strip 16 engages in a longitudinally displaceable manner with the mounting groove 15 of the guide shaft, which mounting groove has a T-shaped configuration.

Towards the connection area 5, the guide shaft 3 has, in the area of its guiding surface 13, a second mounting groove 20, which has a T-shaped configuration and to which an insertion groove 21 with a wide configuration is likewise connected distally. In the corresponding axial area, a first coupling element 22 with a T-shaped configuration is provided on the lower sliding surface 14 of the punching slide 8, which coupling element correspondingly engages in a longitudinally displaceable manner with the mounting groove 20 in the normal operating state. In order to be able to engage this coupling element 22 with the insertion groove 21, the punching slide 8 is placed onto the guide shaft 3 in a position located offset to the guide shaft 3 towards arrow 12, so that the coupling element 22 protrudes into the insertion groove 21. By subsequent adjusting of the punching slide 8 in the direction of arrow 12, the T-shaped coupling element 22 thus engages with the T-shaped mounting groove 20, as this is likewise the case for the guide strip 16 and the mounting groove 15.

In the embodiment variant shown, the base body 2 forms two side walls 25, 26, between which the actuating lever from FIG. 1 with a corresponding adjusting lever (not shown in the drawing) is mounted pivotably, in the connection area 5 between the guide shaft 3 and the partially visible handle 4. Towards the upper guiding surface 13, the two side walls 25 and 26 have each a distally open longitudinal groove 27 and 28, respectively, with which a second T-shaped coupling element 29 can be engaged. In this connection, the punching slide 8 is positioned on the guide shaft 3 in a mounting position arranged offset to the guide shaft 3 towards arrow 12 and adjusted in the direction of arrow 12. The T-shaped coupling element 29 thereby engages with the longitudinal grooves 27 and 28 with its two laterally protruding guide webs 30 and 31.

Furthermore, it can be seen from FIG. 2 that the two coupling elements 22 and 29 have a distance from one another in the axial direction of arrow 12, and that the punching slide 8 has on the bottom a mounting groove 32, which extends between the two coupling elements 22 and 29 in the present exemplary embodiment, the function of which will be explained in detail later. Furthermore, the coupling element 22 has a mounting hole 33, into which a guide pin can be inserted. The coupling element 29 has a hole 34, which is configured in the present exemplary embodiment as a through hole 34 and which can likewise be coupled with the above-mentioned guide pin. This will be explained in detail below.

Furthermore, it can be seen from FIG. 2 that the two side walls 25 and 26 of the base body 2 and of the connection area 5 have two additional longitudinal grooves 40 and 41, which are distally limited towards the handle 4 and form a type of distal stop, vertically "beneath" the two longitudinal grooves 27 and 28 towards the mounting hole 35 of the connection area. These two longitudinal grooves 40 and 41 open into the insertion groove 21, so that a corresponding securing element can be inserted into these longitudinal grooves 40 and 41 via the insertion groove 21.

Figures 3, 4:
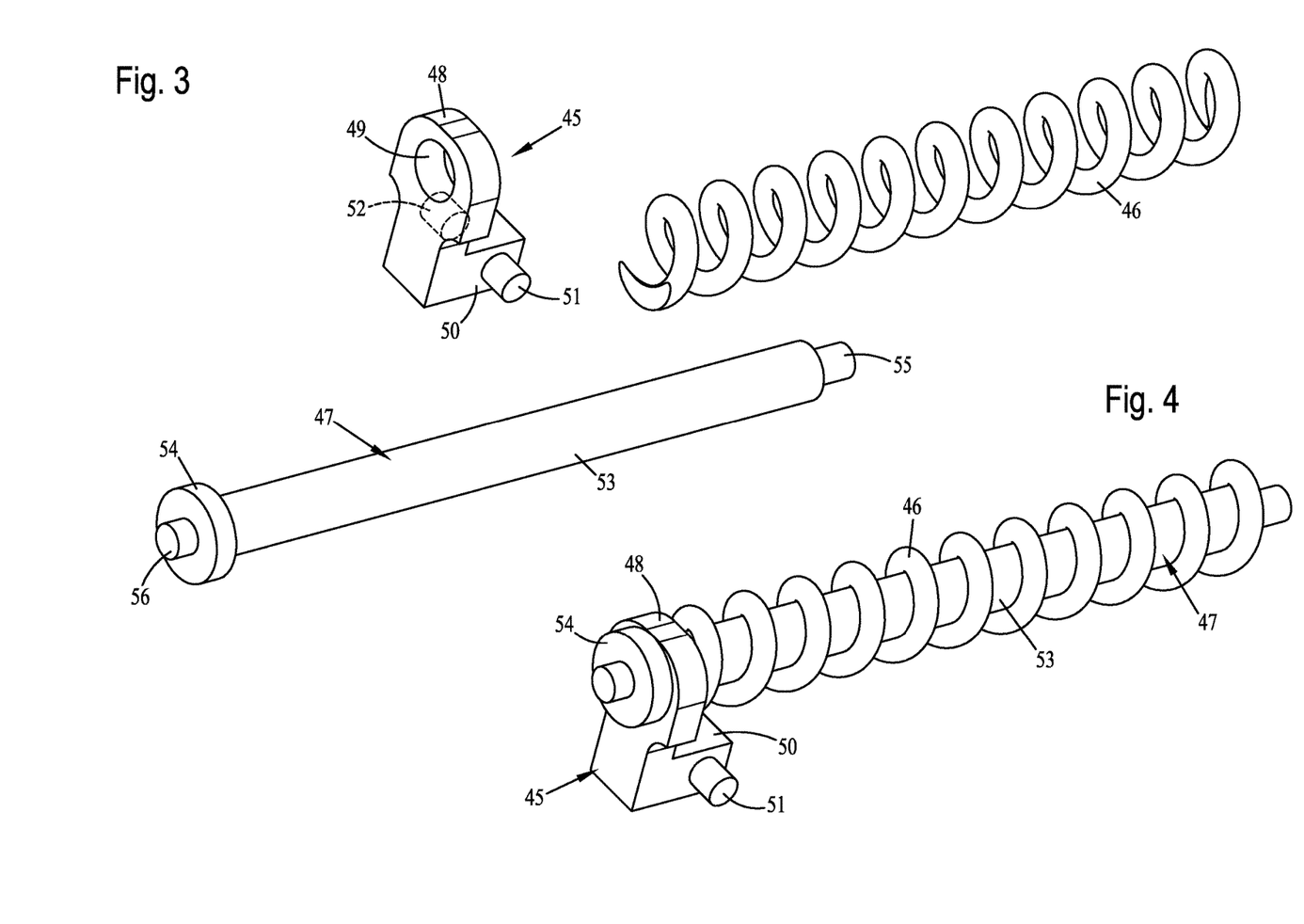
FIG. 3 is a perspective exploded view showing a securing element, a restoring spring configured as a compression coil spring, as well as a guide pin.
FIG. 4 is a perspective view showing the components from FIG. 3 in an assembled state.

FIG. 3 shows a perspective view of such a securing element 45 along with an axial compression spring 46 as well as with a guide pin 47 in a perspective exploded view. The securing element 45 forms a plate-like bearing section 48 directed vertically "upwards," which has a mounting hole 49. A guide web 50, which runs transversely to the bearing section 48 and extends proximally forwards starting from the bearing section, is provided on the bottom at the bearing section 48 in the exemplary embodiment shown. The guide web 50 has two laterally protruding positive-locking elements 51 and 52 which have a pin-like configuration. The securing element 45 can be inserted in a fitting manner between the two side walls 25, 26 of the base body 2, as will be explained in detail later.

The guide pin 47 forms a central, cylindrical mounting section 53, which is limited in its distal end area by a circumferential, radially expanded stop collar 54 in the present exemplary embodiment. In its proximal end area located opposite this stop collar 54, the mounting section 53 has a plug pin 55, which has a radially tapered configuration in the present exemplary embodiment. In axial, distal extension to the stop collar 54, located axially opposite this plug pin 55, the guide pin 47 forms a cylindrical locking pin 56, which likewise has a radially tapered configuration.

As can be seen from FIG. 4, the securing element 45 with the mounting hole 49 of its bearing section 48 can be pushed onto the mounting section 53 of the guide pin 47 and can correspondingly be brought into contact with the stop collar 54 of the guide pin 47. In this case, the guide web 50 of the securing element 45 with its two positive-locking elements 51 and 52 (only the positive-locking element 51 is visible in FIG. 4) has a distance to the mounting section 53 of the guide shaft or guide pin 47. After the securing element 45 with its bearing section 48 is pushed onto the mounting section 53 of the guide pin 47, the axial compression spring 46 can likewise be attached to the mounting section 53 of the guide pin 47. The perspective view of FIG. 4 shows this assembled state. In this fully assembled state, the guide pin 47 together with the axial compression spring 46 as well as with the securing element 45 can be inserted on the bottom at the punching slide 8 between the two coupling elements 22 and 29.

Figure 5:
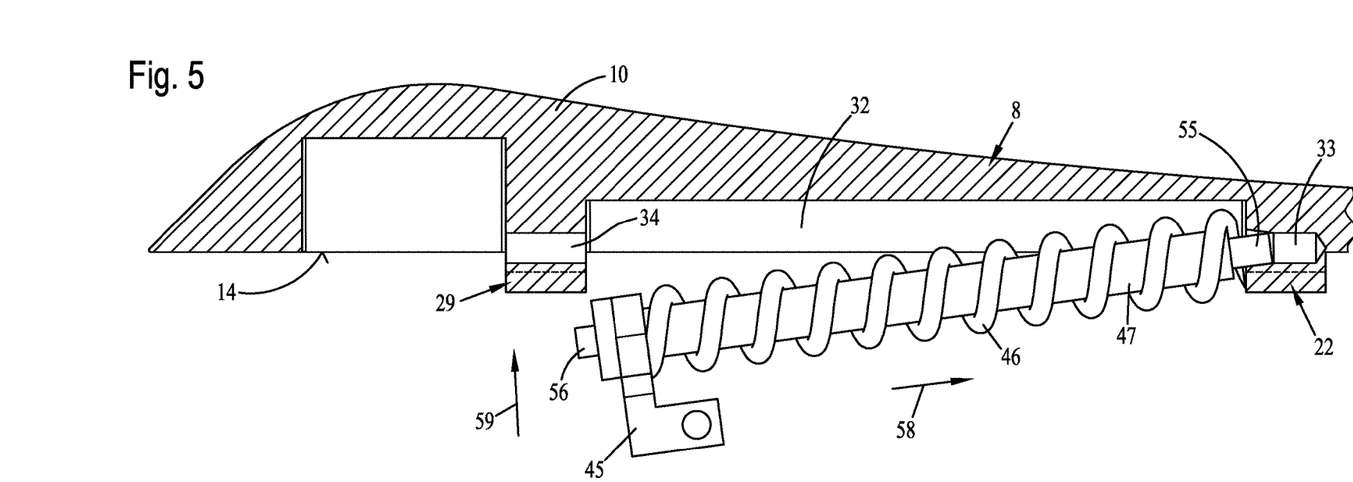
FIG. 5 is a vertical sectional view through the distal end area of the punching slide together with the assembled components according to FIG. 4 immediately before assembly on the punching slide in a state in contact with the punching slide.

To this end, FIG. 5 shows a vertical section of the punching slide 8 in its distal end area 10. In this distal end area 10 are arranged the two coupling elements 22 and 29, which protrude vertically downwards over the lower sliding surface 14 of the punching slide 8. Furthermore, the mounting hole 33 as well as the hole 34 configured as a through hole of the coupling element 22 or 29 can be seen from FIG. 5, on the one hand. For inserting the guide pin 47 together with the pushed-on axial compression spring 46 as well as with the assembled securing element 45, the guide pin 47 is at first engaged with the mounting hole 33 by its proximal plug pin 55, as this can be seen from FIG. 5. Then, the guide pin 47 is pushed further into the mounting hole 33 in the direction of arrow 58 under compression of the axial compression spring 46 until the locking pin 56 thereof can be adjusted in the direction of arrow 59 in the mounting groove 32 of the distal coupling element 29. The mounting hole 33 may have a slightly conical configuration for positioning and pushing in the plug pin 55, as this is shown in FIG. 5.

As soon as the locking pin 56 is aligned with the through hole 34 of the coupling element 29 and the guide pin 47 is released, the guide pin 47 is in turn adjusted towards arrow 58 because of the spring action of the axial compression spring 46, so that the locking pin 56 engages the through hole 34 of the coupling element 29 in a positive-locking manner. Thus, the guide pin 47 is assembled in the area between the two coupling elements 22 and 29 on the punching slide 8 together with the axial compression spring 46 as well as with the securing element 45. In this assembled state, the axial compression spring 46 is partially mounted in the mounting groove 32 extending between the two coupling elements 22 and 29. Together with the two coupling elements 22 and 29, this mounting groove 32 forms a stop each, at which the axial compression spring 46 is axially both proximally and distally supported.

Figure 6:
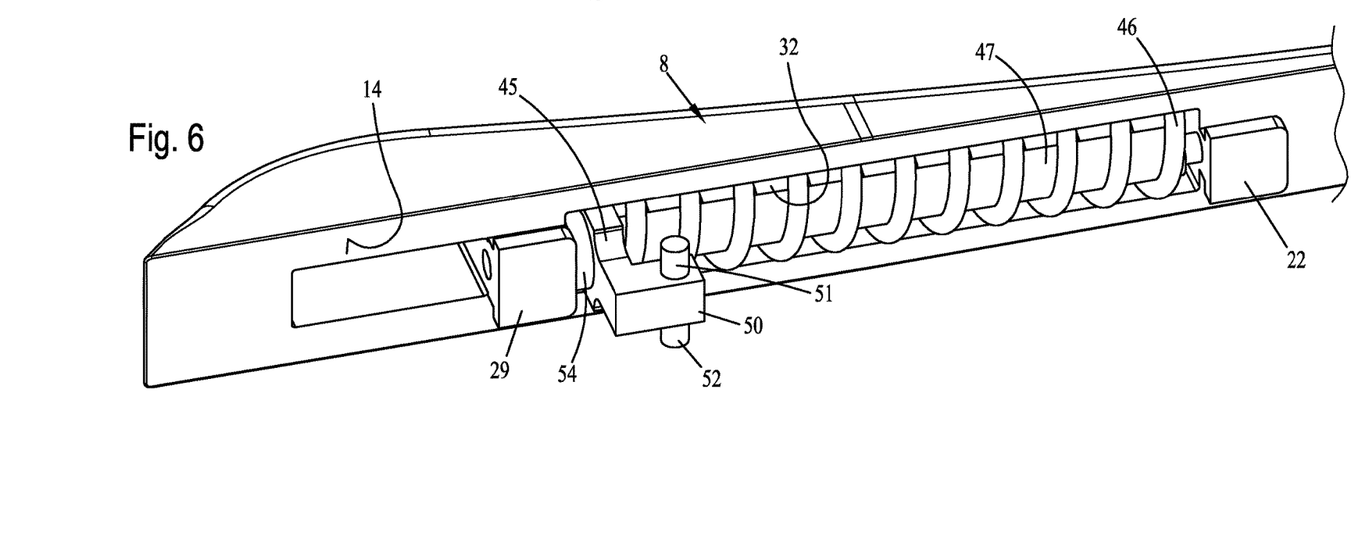
FIG. 6 is a perspective view of the distal end area of the punching slide in perspective bottom view with the components from FIG. 4 in an assembled state on the punching slide.

The perspective bottom view of FIG. 6 shows this fully assembled "operating position."

It can be seen that the axial compression spring 46 is mounted together with the guide pin 47 between the two coupling elements 22 and 29 and partially protrudes into the mounting groove 32 of the punching slide 8. The securing element 45 is mounted in a clamping manner between the distal end of the axial compression spring and the radially expanded stop collar 54 and projects downwards over the lower sliding surface 14 of the punching slide 8, wherein in this position in the normal operating state, the two positive-locking elements 51 and 52 can engage in a longitudinally displaceable manner with the two longitudinal grooves 40 and 41 of the connection area 5 of the base body 2 of the bone punch 1 described in regard to FIG. 2.

In order to be able to engage the securing element 45 with its two positive-locking elements 51 and 52 with the two inner longitudinal grooves 40 and 41 of the two side walls 25 and 26 of the base body 2, the securing element 2 is inserted into the insertion groove 21 as an "individual part" first without the guide pin 47 and without the axial compression spring 46, which can be seen from FIG. 2. In this case, the two positive-locking elements 51 and 52 reach into the vertical area of the two proximally "open" longitudinal grooves 40 and 41 opening into the insertion groove 21 and may thus be engaged with these two longitudinal grooves 40 and 41 towards arrow 12 by means of displacing in the distal direction.

Figure 7:
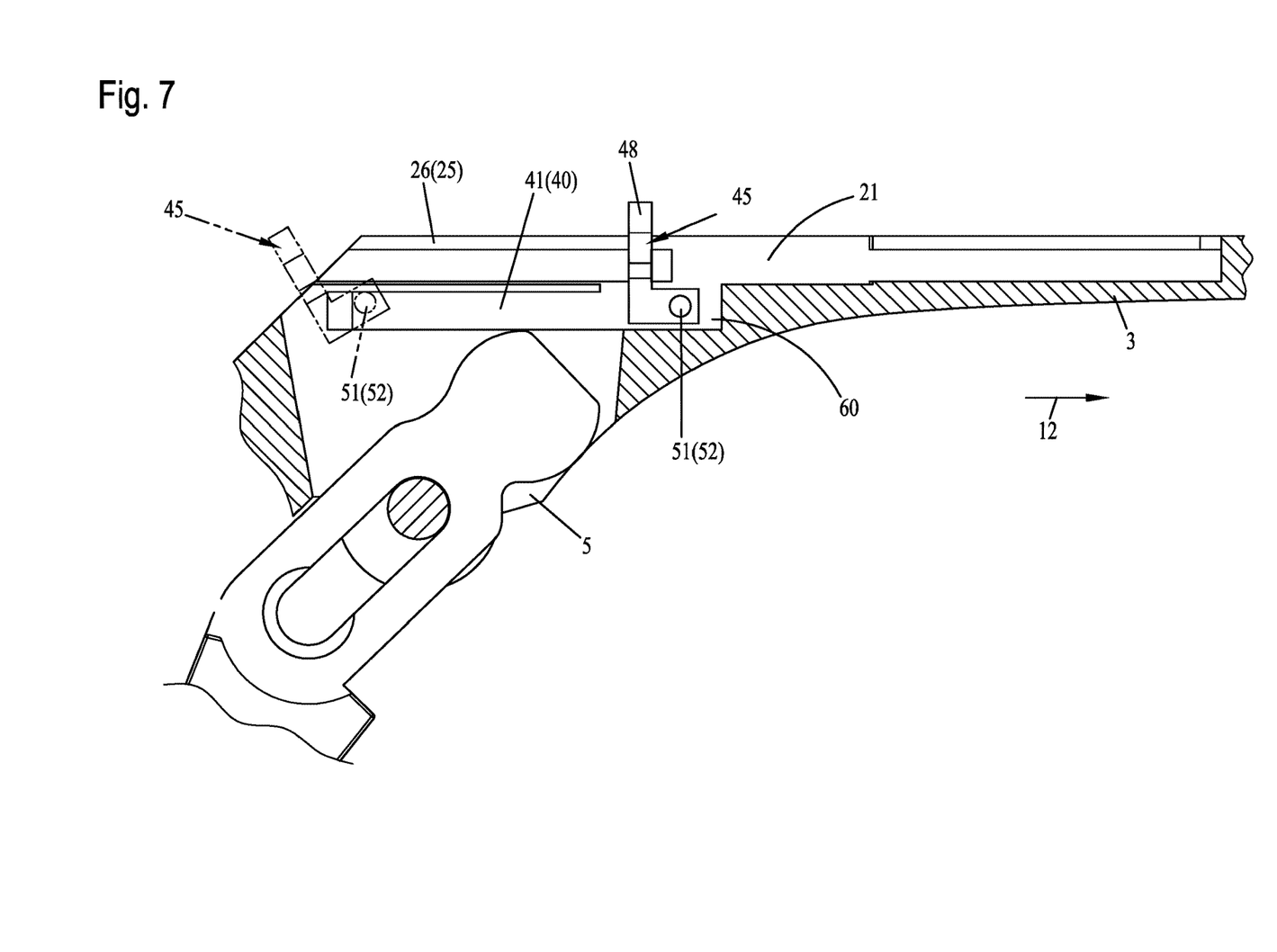
FIG. 7 is a vertical sectional view through the connection area between the guide pin and the handle with inserted adjusting lever of the actuating lever as well as inserted securing element.

For this, FIG. 7 shows the securing element 45 with its mounting shaft 48 as well as with its guide web 50 in solid lines in the state inserted into the insertion groove 21. The insertion groove 21 has an offset configuration in the present exemplary embodiment and has a recessed mounting section 60, which is offset inwards or downwards and into which the two longitudinal grooves 40 and 41 open and into which the securing element 45 with its guide webs 50 is inserted. By displacing the securing element 45 towards arrow 12, the guide web 50 with its two positive-locking elements 51, 52 engages with the longitudinal grooves 40 and 41, wherein only the longitudinal groove 41 of the "rear" side wall 26 can be seen in FIG. 7.

After the securing element 45 has been brought into the "rear" distal end position shown in phantom lines in FIG. 7, the securing element 45 can be brought, by pivoting about its positive-locking elements 51, 52, into an angular position in relation to the connection area 5, in which the securing element 45 can be brought into connection with the guide pin 47 as well as the axial compression spring 46, as this was shown and described in regard to FIG. 4. Since the securing element, especially with its guide web, is inserted in a fitting manner between the two side walls 25 and 26, the securing element cannot be rotated about an axis lying in the bearing section 48.

In this case, the distance of the two side walls 25 and 26 is measured such that in particular the axial compression spring 46 is accommodated between them. Thus, it is ensured that the guide pin 47 and the axial compression spring 46 may also be engaged with the securing element 45, as this can be seen from the sectional view of FIG. 8.

Figure 8:
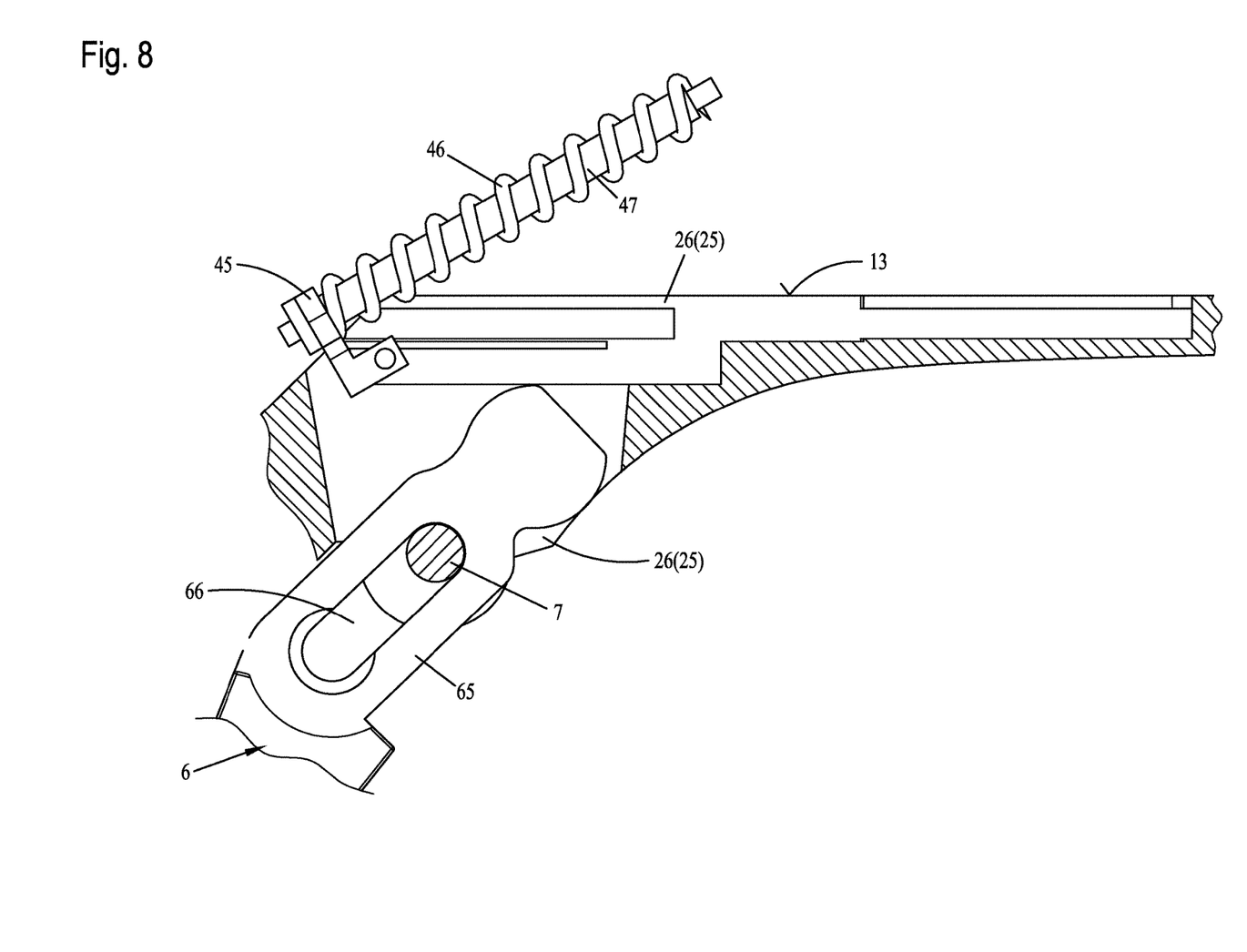
FIG. 8 is the view from FIG. 7 together with the securing element from FIG. 3 arranged in the distal end area of the connection area, as well as the guide pin interacting with the securing element, as well as the axial compression spring placed on the guide pin.

Furthermore, it can also be seen from FIG. 8 that the actuating lever 6 has an adjusting lever 65, which is mounted in the area of the two side walls 25 and 26, wherein only the "rear" side wall 26 can be seen in FIG. 8. In the area of these two side walls 25 and 26, the mounting pin 7 that was mentioned in regard to FIG. 1 can be seen, at which the actuating lever 6 with its adjusting lever 65 is pivotably mounted via an elongated hole 66 and can be adjusted radially to the mounting pin 7 as needed.

The precise configuration of the mounting as well as of the mounting pin 7 and the configuration of the adjusting lever 65 can be taken from DE 20 2004 017 974 U1 (corresponding to U.S. Pat. No. 7,655,020), especially from the description on the drawing FIGS. 20 through 23. The fundamental, functional and structural configuration of the mounting is also provided in the subject of the invention, so that reference is made to the full extent to this description of said patent and this description is also incorporated herein as content of the present application.

It should be noted at this point, however, that the actuating lever may also be otherwise mounted rotatably and adjustably on the base body, as this is likewise known from the state of the art. It can only be ensured that the adjusting lever can be disengaged from the punching slide by means of corresponding manipulation in order to be able to separate the punching slide from the guide shaft and the base body.

As can be further seen from FIG. 8, in its state of being engaged with the securing element 45, the guide pin 47 runs together with the axial compression spring 46 at first transversely to the upper guiding surface 13 of the guide shaft 3. In this angular position, the punching slide 8 from FIG. 2, as described in regard to FIGS. 5 and 6, can now be engaged with the guide pin 47. Ultimately, this means that the punching slide 8 is suspended on the guide pin 7 or "locked" on same in a simple manner.

Figure 9:
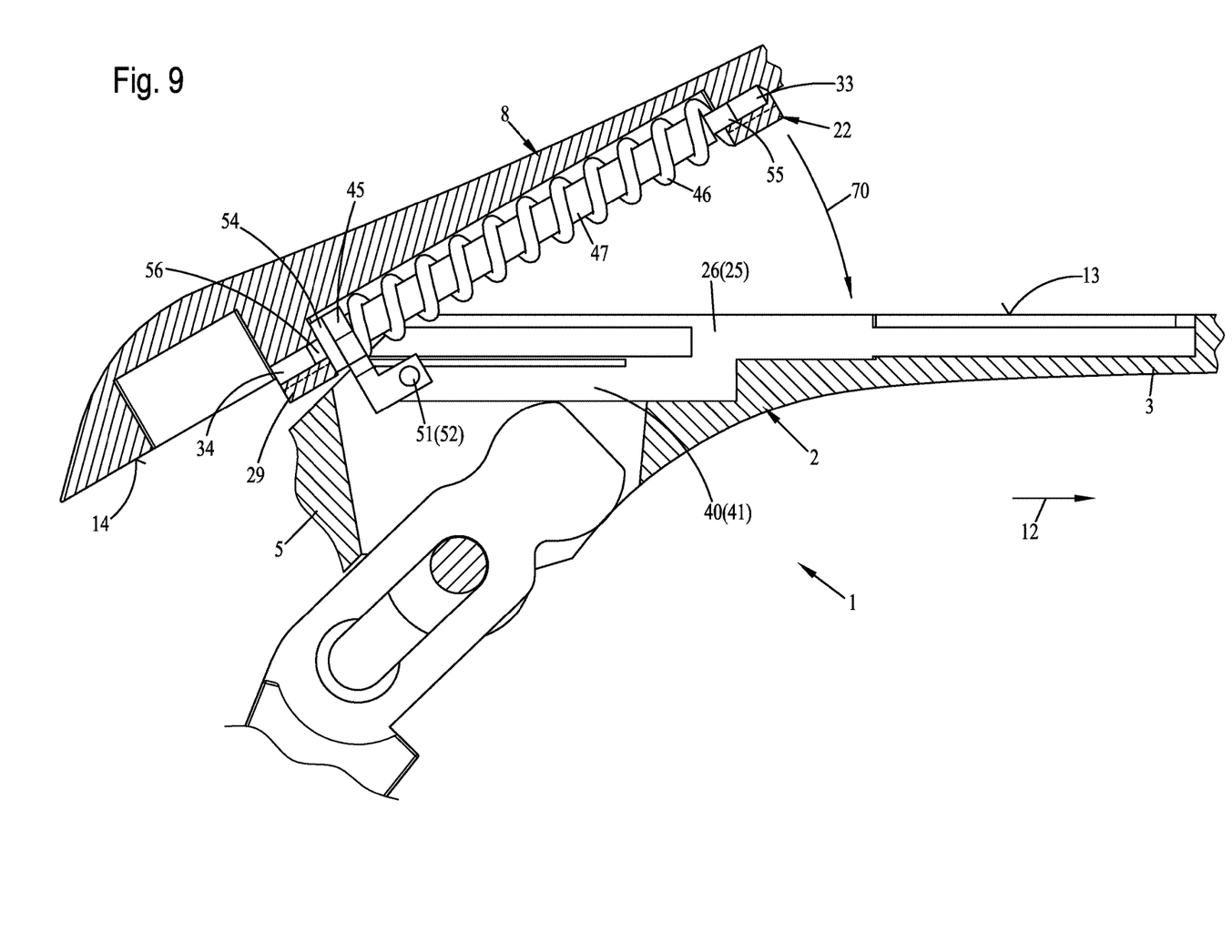
FIG. 9 is the vertical sectional view from FIG. 8 with the punching slide assembled on the guide pin.

The sectional view of FIG. 9 shows this fully assembled state.

As can be seen from the sectional view of FIG. 9, the guide pin 47 with its plug pin 55 is inserted into the mounting hole 33 of the coupling element 22. The axial compression spring 46 is mounted on the mounting section 53 of the guide pin 47. This axial compression spring is supported proximally at the coupling element 22 and fixes the securing element at the distal stop collar 54 of the guide pin 47. The guide pin 47 is locked with its locking pin 56 in the through hole 34 of the distal coupling element 29.

Thus, it can be seen from FIG. 9 that the securing element 45 interacts with the punching slide 8 in a fixed manner via the guide pin 47 as well as the axial compression spring 46. Because of the positive-locking, displaceable engagement of its two positive-locking elements 51 and 52, of which only the positive-locking element 52 is visible in FIG. 9, with the two longitudinal grooves 40 and 41, of which only the rear longitudinal groove 41 of the rear side wall 26 can be seen in FIG. 9, the punching slide 8 is thus securely connected to the base body 2 of the bone punch 1 via the securing element 45.

As can be seen from FIG. 1, the base body 2 in the connection area 5, especially in the area of the upper guiding surface 13 and the punching slide 8 in the area of its sliding surface 14, have at least approximately the same width in the distal end area, so that in the position shown in FIG. 9, the punching slide 8 cannot be adjusted in the direction of arrow 12 and the secure engagement of the securing element 45 with the longitudinal grooves 40 and 41 by its two positive-locking elements 51 and 52 cannot thus be severed. Since the longitudinal grooves 40 and 41 are limited distally, the securing element 45 with its two positive-locking elements 51 and 52 cannot be pushed out of the two longitudinal grooves 40 and 41 towards arrow 12.

If the punching slide 8 shall be entirely detached from the base body 2, then, for example, with a corresponding auxiliary tool, the guide pin 47 with its locking pin 56 can be disengaged from the through hole 34 by simple adjusting along the punching slide 8, so that the punching slide 8 can be removed in a simple manner from the securing element 45 and thus from the base body 2.

Figure 10:
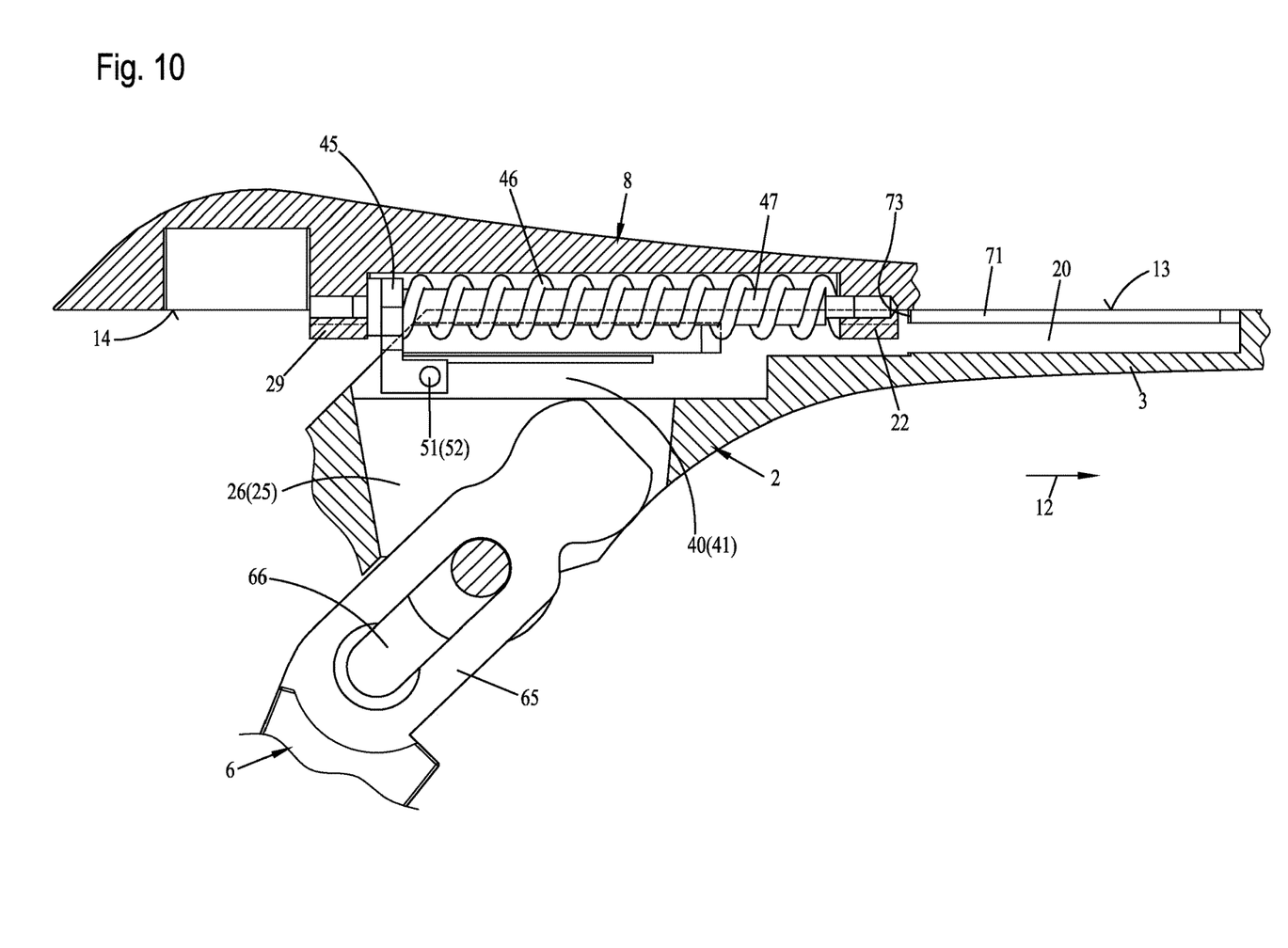
FIG. 10 is the view from FIG. 9 with the punching slide in a distally retracted position lying on the guide pin.

In order to bring the punching slide 8 into its normal operating position shown in FIG. 1, this is at first pivoted out of the pivoting position shown in FIG. 9 in the direction of arrow 70 about the positive-locking elements 51, 52 until the punching slide 8 with its lower sliding surface 14 comes into contact with the upper guiding surface 13 of the base body 2 or of the guide shaft 3, as this can be seen from FIG. 10.

It can be seen that the punching slide 8 with its lower sliding surface 14 lies flatly on the guiding surface 13 of the base body 2 or of the guide shaft 3. Furthermore, the mounting groove 20 can be seen from FIG. 10. With reference to FIG. 2, it can be seen that this mounting groove 20 has a T-shaped configuration and has an inwards protruding slide web 71 or 72 each on both sides, of which only the slide web 71 can be seen in FIG. 10. These slide webs 71, 72 form each distally a type of stop 73 and 74, respectively, of which only the stop 73 can be seen in FIG. 10.

If the punching slide 8 is now adjusted together with the mounted guide pin 47, with the axial compression spring 46 as well as with the securing element 45 in the direction of arrow 12 (FIG. 10), then the coupling element 22 engages with the mounting groove 20 and extends behind the two slide webs 71 and 72 described in regard to FIG. 2 because of its T-shaped configuration, on the one hand. After a certain path of adjustment in the direction of arrow 12, the axial compression spring 46 with its proximal end comes into contact with the two stops 73 and 74 of the slide webs 71 and 72, which can be seen in FIG. 2. By further adjustment of the punching slide 8 in relation to the base body 2 in the direction of arrow 12, the guide pin 47, the securing element 45 as well as the two coupling elements 22 and 29 are also inevitably adjusted in the direction of arrow 12, as a result of which a compression of the axial compression spring 46 is brought about, since this spring crops out at the two stops 73, 74 with its proximal end. At the same time, the securing element 45 with its two positive-locking elements 51 and 52 slides along the longitudinal grooves 40 and 41. The coupling element 29 engages with the two longitudinal grooves 27 and 28 because of its T-shaped configuration, so that a removal of the punching slide 8 from the base body 2 is no longer possible.

After the punching slide 8 has been brought into its "normal" operating position according to FIG. 1, the actuating lever 6 with its adjusting lever 65 can be adjusted via its elongated hole 66 between the two side walls 25 and 26, as this is known from DE 20 2004 017 974 U1.

Figure 11:
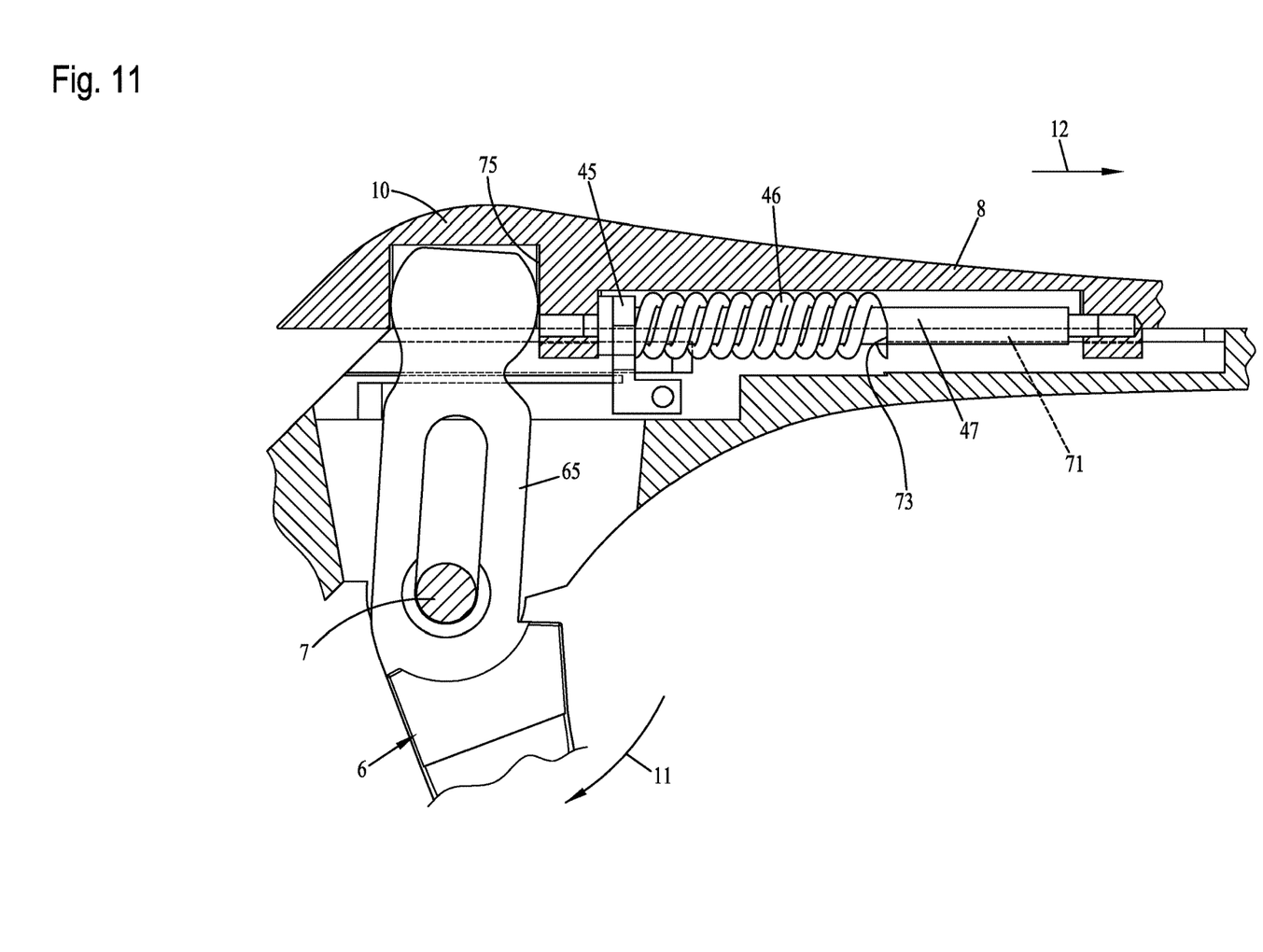
FIG. 11 is the view from FIG. 10 with the punching slide as well as the actuating lever with an adjusting lever in a normal operating position in the vertical section.

In this case, the adjusting lever 65 engages with a corresponding recess 75 provided on the bottom in the distal end area 10 of the punching slide 8, as this can be seen from the sectional view of FIG. 11.

If the actuating lever 6 with its adjusting lever 65 is now pivoted about the mounting pin 7 in the direction of arrow 11, then this brings about an adjustment of the punching slide 8 in the direction of arrow 12, as this is known from the state of the art, especially from DE 20 2004 017 974 U1.

With regard to the other mode of operation of the bone punch according to the present invention, reference is likewise made to this patent DE 20 2004 017 974 U1, and especially as concerns the configuration of the proximal end area both of the punching slide 8 and of the guide shaft 3.

It should also be noted at this point that, in principle, the configuration of the punching slide 8 with its securing element 45 can also be used when no axial compression spring 46 with guide pin 47 is present. This configuration could thus also, in principle, apply, for example, to the subject of DE 10 2009 056 099 B4.

The detachable assembly of the securing element 45 could in this case be carried out at the distal coupling element 29, for example, by means of a correspondingly arranged screw connection, so that the securing element 45 also interacts detachably with the punching slide 8 in such a case (not shown in the drawing). This configuration would be, however, somewhat more complicated, but fundamentally possible in relation to the assembly process of the punching slide.

The configuration of the bone punch 1 according to the present invention is advantageous in that especially in the normal operating state of the bone punch 1, the securing element 45 is arranged completely within the punching slide 8 and within the base body 2 of the bone punch 1 and is thus protected against external effects. In the normal operation of the bone punch 1, the securing element 45 always remains completely inaccessible from outside in the punching slide 8 and the base body 2, so that there is no risk of injury for the operator, especially during actuation of the bone punch 1.

Thus, the bone punch 1 according to the present invention with its securing element 45 and the corresponding longitudinal grooves 40, 41 can be handled in an equally simple manner as the bone punch from DE 20 2004 017 974 U1. Since the securing element 45 and the corresponding longitudinal grooves 40 and 41 are arranged completely within the punching slide 8 and within the base body 2, there is also no risk of contaminations of these components during use here.

As described above, the punching slide 8, especially by using the guide pin 47 together with the axial compression spring 46, may also be separated from these two components in a simple manner, so that a separation from the securing element 45 also takes place automatically and inevitably, as described above.

The bone punch 1 according to the present invention with the securing element 45 can thus also be completely disassembled and also reassembled in a simple manner as needed.

While specific embodiments of the invention have been shown and described in detail to illustrate the application of the principles of the invention, it will be understood that the invention may be embodied otherwise without departing from such principles.

What is claimed is:

1. A bone punch comprising:
   a base body comprising a guide shaft and a handle arranged fixed and angled on the guide shaft;
   a punching slide supported adjustably along the guide shaft on an upper guiding surface of the guide shaft, the guiding surface being located opposite a handle side;
   guide elements, having a T-shaped profile, associated with the punching slide;
   a restoring spring;
   an actuating lever pivotably mounted to the guide shaft in a connection area of the handle between two side walls formed by the guide shaft of the base body, which are spaced apart from one another, wherein the actuating lever forms an adjusting lever configured for the actuating lever operatively interacting with the punching slide for adjustment of the punching slide along the guide shaft against the spring action of the restoring spring and wherein the punching slide is guided adjustably along on the guide shaft via the guide elements, which engage one another in a positive-locking manner and are detachable by longitudinal displacement; and a securing element connected to the punching slide at a distal end area of the punching slide, the securing element extending between the two side walls in an assembled state of the punching slide on the guide shaft and the securing element having two laterally protruding positive-locking elements and each of the side walls is provided with an inner, distally limited longitudinal groove running in a longitudinal direction of the guide shaft, each positive-locking element being inserted longitudinally displaceably in a respective one of said longitudinal grooves.

2. A bone punch in accordance with claim 1, wherein the securing element further comprises a bearing section extending toward the punching slide, the bearing section of the securing element detachably interacting with the punching slide.

3. A bone punch in accordance with claim 2, wherein:
a guide pin is associated with the punching slide and in the assembled state, is removably inserted proximally into a mounting hole of the punching slide and distally into a second hole of the punching slide;
the restoring spring comprises an axial compression spring arranged on the guide pin and in the assembled state is partly arranged in a lower mounting groove of the punching slide;
the axial compression spring is axially supported proximally at a first stop of the punching slide in case of the punching slide being removed from the guide shaft;
the axial compression spring is axially supported indirectly or directly at a distal second stop of the punching slide; and
the securing element is mounted with the bearing section between the distal end of the axial compression spring and the second stop.

4. A bone punch in accordance with claim 3, wherein:
in a guide pin distal end area, the guide pin has a radially protruding stop collar, via which the axial compression spring is indirectly axially supported at the distal second stop; and
the bearing section of the securing element is mounted on the guide pin between the distal end of the axial compression spring and the stop collar of the guide pin.

5. A bone punch in accordance with claim 3, wherein:
the first stop is part of one of the guide elements, forming a first coupling element of the punching slide, the first coupling element having the T-shaped profile and projecting beyond the sliding surface of the punching slide toward the guiding surface of the guide shaft and engaging in a longitudinally displaceable manner with one of the other one of the guide elements forming a mounting groove of the guide shaft in the assembled state, which mounting groove has the T-shaped profile;
the distal second stop is a part of one of the guide elements, forming a second coupling element of the punching slide, which coupling element has the T-shaped profile configuration and projects beyond the sliding surface of the punching slide toward the guiding surface of the guide pin and engages in a longitudinally displaceable manner with inner longitudinal grooves arranged laterally in the side walls in the assembled state; and
the first stop and the second stop are also part of the mounting groove of the punching slide for the axial compression spring.

6. A bone punch in accordance with claim 5, wherein:
the punching slide is provided in an area of the first coupling element with a mounting hole, into which the guide pin can be inserted with a proximal plug pin, which has a radially tapered configuration;
the punching slide has a through hole in an area of the distal second coupling element;
the guide pin has a distal axial extension of the stop collar and has a locking pin which has a radially tapered configuration, with which the guide pin can be engaged in a positive-locking manner due to an axial adjustment of the guide pin in the mounting hole against the spring action of the axial compression spring positioned on the guide pin with the through hole in the area of the second coupling element.

7. A bone punch in accordance with claim 1, wherein each of the side walls comprises an open longitudinal groove, the open longitudinal groove of one of the side walls being located at a position above the inner, distally limited longitudinal groove of the one of the side walls, the open longitudinal groove of another one of the side walls being located at a position above the inner, distally limited longitudinal groove of the another one of the side walls, the open longitudinal groove of the one of the side walls receiving at least a portion of at least one of the guide elements, the open longitudinal groove of the another one of the side walls receiving at least another portion of the at least one of the guide elements.

8. A bone punch comprising:
a base body comprising a handle and a guide shaft, the guide shaft comprising a first wall defining a first inner, distally limited longitudinal groove and a second wall defining a second inner, distally limited longitudinal groove, the first wall being located at a spaced location from the second wall, the first inner, distally limited longitudinal groove and the second inner, distally limited longitudinal groove extending in a longitudinal direction of the guide shaft, the handle being arranged fixed and angled on the guide shaft;
a punching slide supported adjustably along the guide shaft on an upper guiding surface of the guide shaft, the guiding surface being located opposite a handle side;
guide elements, having a T-shaped profile, associated with the punching slide;
a restoring spring;
an actuating lever pivotably mounted to the guide shaft in a connection area of the handle between the first side wall and the second side wall, wherein the actuating lever forms an adjusting lever configured for the actuating lever operatively interacting with the punching slide for adjustment of the punching slide along the guide shaft against the spring action of the restoring spring and wherein the punching slide is guided adjustably along on the guide shaft via the guide elements, which engage one another in a positive-locking manner and are detachable by longitudinal displacement; and
a securing element connected to the punching slide at a distal end area of the punching slide, the securing element extending between the first side wall and the second side wall in an assembled state of the punching slide on the guide shaft and the securing element having a first laterally protruding positive-locking element and a second laterally protruding positive-locking element, the first laterally protruding positive-locking element being inserted longitudinally displaceably in the first inner, distally limited longitudinal groove, the second laterally protruding positive-locking element being inserted longitudinally displaceably in the second inner, distally limited longitudinal groove.

9. A bone punch in accordance with claim 8, wherein the securing element further comprises a bearing section extending toward the punching slide, the bearing section of the securing element detachably interacting with the punching slide.

10. A bone punch in accordance with claim 9, wherein:
a guide pin is associated with the punching slide and in the assembled state, is removably inserted proximally into a mounting hole of the punching slide and distally into a second hole of the punching slide;
the restoring spring comprises an axial compression spring arranged on the guide pin and in the assembled state is partly arranged in a lower mounting groove of the punching slide;
the axial compression spring is axially supported proximally at a first stop of the punching slide in case of the punching slide being removed from the guide shaft;
the axial compression spring is axially supported indirectly or directly at a distal second stop of the punching slide; and
the securing element is mounted with the bearing section between the distal end of the axial compression spring and the second stop.

11. A bone punch in accordance with claim 10, wherein:
in a guide pin distal end area, the guide pin has a radially protruding stop collar, via which the axial compression spring is indirectly axially supported at the distal second stop; and
the bearing section of the securing element is mounted on the guide pin between the distal end of the axial compression spring and the stop collar of the guide pin.

12. A bone punch in accordance with claim 10, wherein:
the first stop is part of one of the guide elements, forming a first coupling element of the punching slide, the first coupling element having the T-shaped profile and projecting beyond the sliding surface of the punching slide toward the guiding surface of the guide shaft and engaging in a longitudinally displaceable manner with one of the other one of the guide elements forming a mounting groove of the guide shaft in the assembled state, which mounting groove has the T-shaped profile;
the distal second stop is a part of one of the guide elements, forming a second coupling element of the punching slide, which coupling element has the T-shaped profile configuration and projects beyond the sliding surface of the punching slide toward the guiding surface of the guide pin and engages in a longitudinally displaceable manner with inner longitudinal grooves arranged laterally in the side walls in the assembled state; and
the first stop and the second stop are also part of the mounting groove of the punching slide for the axial compression spring.

13. A bone punch in accordance with claim 12, wherein:
the punching slide is provided in an area of the first coupling element with a mounting hole, into which the guide pin can be inserted with a proximal plug pin, which has a radially tapered configuration;
the punching slide has a through hole in an area of the distal second coupling element;
the guide pin has a distal axial extension of the stop collar and has a locking pin which has a radially tapered configuration, with which the guide pin can be engaged in a positive-locking manner due to an axial adjustment of the guide pin in the mounting hole against the spring action of the axial compression spring positioned on the guide pin with the through hole in the area of the second coupling element.

14. A bone punch in accordance with claim 8, wherein each of the first side wall and the second side wall comprises an open longitudinal groove, the open longitudinal groove of the first side wall being located at a position above the first inner, distally limited longitudinal groove, the open longitudinal groove of the second side wall being located at a position above the second inner, distally limited longitudinal groove, the open longitudinal groove of the first side wall receiving at least a portion of at least one of the guide elements, the open longitudinal groove of the second side wall receiving at least another portion of the at least one of the guide elements.

15. A bone punch comprising:
a base body comprising a handle and a guide shaft comprising a plurality of side walls, each of the side walls defining an inner, distally limited longitudinal groove, each inner, distally limited longitudinal groove extending in a longitudinal direction of the guide shaft, the handle being arranged fixed and angled on the guide shaft;
a punching slide supported adjustably along the guide shaft on an upper guiding surface of the guide shaft, the guiding surface being located opposite a handle side;
guide elements, having a T-shaped profile, associated with the punching slide;
a restoring spring;
an actuating lever pivotably mounted to the guide shaft in a connection area of the handle between one of the plurality of side walls and another one of the plurality of side walls, wherein the actuating lever forms an adjusting lever configured for the actuating lever operatively interacting with the punching slide for adjustment of the punching slide along the guide shaft against the spring action of the restoring spring and wherein the punching slide is guided adjustably along on the guide shaft via the guide elements, which engage one another in a positive-locking manner and are detachable by longitudinal displacement; and
a securing element connected to the punching slide at a distal end area of the punching slide, the securing element extending between the one of the plurality of side walls and the another one of the plurality of side walls in an assembled state of the punching slide on the guide shaft and the securing element having a first laterally protruding positive-locking element and a second laterally protruding positive-locking element, the first laterally protruding positive-locking element being inserted longitudinally displaceably in the inner, distally limited longitudinal groove of the one of the plurality of side walls, the second laterally protruding positive-locking element being inserted longitudinally displaceably in the inner, distally limited longitudinal groove of the another one of the plurality of side walls.

16. A bone punch in accordance with claim 15, wherein the securing element further comprises a bearing section extending toward the punching slide, the bearing section of the securing element detachably interacting with the punching slide.

17. A bone punch in accordance with claim 16, wherein:
a guide pin is associated with the punching slide and in the assembled state, is removably inserted proximally into a mounting hole of the punching slide and distally into a second hole of the punching slide;

the restoring spring comprises an axial compression spring arranged on the guide pin and in the assembled state is partly arranged in a lower mounting groove of the punching slide;

the axial compression spring is axially supported proximally at a first stop of the punching slide in case of the punching slide being removed from the guide shaft;

the axial compression spring is axially supported indirectly or directly at a distal second stop of the punching slide; and the securing element is mounted with the bearing section between the distal end of the axial compression spring and the second stop.

18. A bone punch in accordance with claim 17, wherein:

in a guide pin distal end area, the guide pin has a radially protruding stop collar, via which the axial compression spring is indirectly axially supported at the distal second stop; and the bearing section of the securing element is mounted on the guide pin between the distal end of the axial compression spring and the stop collar of the guide pin.

19. A bone punch in accordance with claim 17, wherein:

the first stop is part of one of the guide elements, forming a first coupling element of the punching slide, the first coupling element having the T-shaped profile and projecting beyond the sliding surface of the punching slide toward the guiding surface of the guide shaft and engaging in a longitudinally displaceable manner with one of the other one of the guide elements forming a mounting groove of the guide shaft in the assembled state, which mounting groove has the T-shaped profile;

the distal second stop is a part of one of the guide elements, forming a second coupling element of the punching slide, which coupling element has the T-shaped profile configuration and projects beyond the sliding surface of the punching slide toward the guiding surface of the guide pin and engages in a longitudinally displaceable manner with inner longitudinal grooves arranged laterally in the side walls in the assembled state; and the first stop and the second stop are also part of the mounting groove of the punching slide for the axial compression spring.

20. A bone punch in accordance with claim 15, wherein each of the plurality of side walls comprises an open longitudinal groove, the open longitudinal groove of the one of the plurality of side walls being located at a position above the inner, distally limited longitudinal groove of the one of the plurality of side walls, the open longitudinal groove of another one of the plurality of side walls being located at a position above the inner, distally limited longitudinal groove of the another one of the plurality of side walls, the open longitudinal groove of the one of the plurality of side walls receiving at least a portion of at least one of the guide elements, the open longitudinal groove of the another one of the plurality of side walls receiving at least another portion of the at least one of the guide elements.

* * * * *